(12) United States Patent
Ehninger et al.

(10) Patent No.: US 11,283,213 B2
(45) Date of Patent: Mar. 22, 2022

(54) CABLE CONNECTION SYSTEMS FOR ELECTROSURGICAL SYSTEMS

(71) Applicant: Megadyne Medical Products, Inc., Draper, UT (US)

(72) Inventors: Michael D. Ehninger, South Jordan, UT (US); Paul R. Borgmeier, Salt Lake City, UT (US); Darcy W. Greep, Herriman, UT (US)

(73) Assignee: Megadyne Medical Products, Inc., Draper, UT (US)

( * ) Notice: Subject to any disclaimer, the term of this patent is extended or adjusted under 35 U.S.C. 154(b) by 1074 days.

(21) Appl. No.: 15/599,279

(22) Filed: May 18, 2017

(65) Prior Publication Data
US 2017/0365948 A1 Dec. 21, 2017

Related U.S. Application Data

(60) Provisional application No. 62/351,822, filed on Jun. 17, 2016.

(51) Int. Cl.
*H01R 13/52* (2006.01)
*A61B 18/16* (2006.01)
(Continued)

(52) U.S. Cl.
CPC ..... *H01R 13/5224* (2013.01); *A61B 18/1206* (2013.01); *A61B 18/16* (2013.01);
(Continued)

(58) Field of Classification Search
CPC .......... A61B 2018/00172; A61B 2018/00178; A61B 18/1206; A61B 2018/1253;
(Continued)

(56) References Cited

U.S. PATENT DOCUMENTS 3,848,164 A * 11/1974 Otte ................. H01R 24/52
439/579
3,895,635 A * 7/1975 Justus ................... A61B 18/16
606/32
(Continued)

FOREIGN PATENT DOCUMENTS

CN 1620270 5/2005
DE 10 2009 012387 9/2010
(Continued)

OTHER PUBLICATIONS

English (Machine) Translation of EP1112720 (Jul. 4, 2001), 31 Pages (Year: 2001).*

*Primary Examiner* — Ronald Hupczey, Jr.
*Assistant Examiner* — Bradford C. Blaise
(74) *Attorney, Agent, or Firm* — Workman Nydegger (57) ABSTRACT

Cable connection systems allow for an electrosurgical return electrode to be simultaneously connected to multiple ESUs. The cable connection systems can include individual return cables for simultaneous connection to each of the ESUs. The cable connection system can also include a junction that joins, connects, or associates the return cables in a manner that allows for the multiple ESU cables to be electrically connected to the return electrode at a single connection point on the return electrode.

31 Claims, 9 Drawing Sheets

(51) Int. Cl.
*A61B 18/12* (2006.01)
*H01R 13/516* (2006.01)
*A61B 18/00* (2006.01)

(52) U.S. Cl.
CPC ....... *H01R 13/516* (2013.01); *H01R 13/5213* (2013.01); *A61B 2018/00178* (2013.01); *A61B 2018/00595* (2013.01); *A61B 2018/00601* (2013.01); *A61B 2018/1253* (2013.01); *A61B 2018/1273* (2013.01); *A61B 2018/162* (2013.01); *A61B 2018/165* (2013.01); *A61B 2018/167* (2013.01); *H01R 2201/12* (2013.01)

(58) Field of Classification Search
CPC ............ A61B 2018/1273; A61B 18/16; A61B 2018/165; A61B 2018/167; H01R 2201/12; H01R 13/516; H01R 13/5213; H01R 13/5224
See application file for complete search history.

(56) References Cited

U.S. PATENT DOCUMENTS

| | | | |
|---|---|---|---|
| 4,094,320 A | 6/1978 | Newton et al. | |
| 4,166,465 A * | 9/1979 | Esty | A61B 18/16 606/32 |
| 4,852,585 A * | 8/1989 | Heath | A61N 1/046 600/397 |
| 5,042,981 A | 8/1991 | Gross | |
| 5,562,503 A * | 10/1996 | Ellman | A61B 18/14 200/51.03 |
| 5,633,578 A * | 5/1997 | Eggers | A61B 18/1206 323/301 |
| 5,695,494 A | 12/1997 | Becker | |
| 6,035,239 A | 3/2000 | Patag et al. | |
| 6,053,910 A * | 4/2000 | Fleenor | A61B 18/16 606/32 |
| 6,083,221 A | 7/2000 | Fleenor et al. | |
| 6,199,784 B1 | 3/2001 | Wang et al. | |
| 6,454,764 B1 | 9/2002 | Fleenor et al. | |
| 6,544,258 B2 | 4/2003 | Fleenor et al. | |
| 6,582,424 B2 | 6/2003 | Fleenor et al. | |
| 6,666,859 B1 | 12/2003 | Fleenor et al. | |
| 6,796,828 B2 | 9/2004 | Ehr et al. | |
| 6,860,881 B2 | 3/2005 | Sturm et al. | |
| 6,892,086 B2 | 5/2005 | Russell | |
| 6,997,735 B2 | 2/2006 | Ehr et al. | |
| 7,166,102 B2 | 1/2007 | Fleenor et al. | |
| 7,169,145 B2 | 1/2007 | Isaacson et al. | |
| 7,182,604 B2 | 2/2007 | Ehr et al. | |
| 7,229,307 B2 | 6/2007 | Ehr et al. | |
| 7,311,560 B2 | 12/2007 | Ehr et al. | |
| 7,367,971 B2 | 5/2008 | Fleenor et al. | |
| 7,473,145 B2 | 1/2009 | Ehr et al. | |
| 7,566,332 B2 | 7/2009 | Jarrard et al. | |
| 7,722,412 B2 | 5/2010 | Ehr et al. | |
| 7,837,680 B2 | 11/2010 | Isaacson et al. | |
| 7,883,507 B2 | 2/2011 | Jarrard et al. | |
| 7,909,819 B2 | 3/2011 | Falkenstein et al. | |
| 7,938,825 B2 | 5/2011 | Sturm et al. | |
| 8,048,068 B2 | 11/2011 | Falkenstein et al. | |
| 8,096,988 B2 | 1/2012 | Jarrard et al. | |
| 8,486,059 B2 | 7/2013 | Schoenman | |
| 8,523,853 B2 | 9/2013 | Dunning | |
| D707,828 S | 6/2014 | Ehninger et al. | |
| 8,758,336 B2 | 6/2014 | Odell et al. | |
| D709,205 S | 7/2014 | Ehninger et al. | |
| 8,876,812 B2 | 11/2014 | Aramayo | |
| 8,932,283 B2 | 1/2015 | Van Wyk et al. | |
| 2001/0029367 A1 | 10/2001 | Fleenor et al. | |
| 2003/0013948 A1 | 1/2003 | Russell | |
| 2003/0040741 A1 * | 2/2003 | Fleenor | A61B 18/16 606/32 |
| 2003/0078572 A1 * | 4/2003 | Pearson | A61B 18/14 606/34 |
| 2003/0181090 A1 | 9/2003 | Ehr et al. | |
| 2004/0256188 A1 * | 12/2004 | Harcourt | H02G 11/02 191/12.2 A |
| 2005/0079752 A1 | 4/2005 | Ehr et al. | |
| 2006/0030195 A1 | 2/2006 | Ehr et al. | |
| 2006/0264921 A1 * | 11/2006 | Deutsch | A61B 18/14 606/32 |
| 2006/0286861 A1 * | 12/2006 | Avevor | A61B 5/04286 439/501 |
| 2007/0111552 A1 | 5/2007 | Ehr et al. | |
| 2008/0033276 A1 | 2/2008 | Ehr et al. | |
| 2008/0050984 A1 | 2/2008 | Ehr et al. | |
| 2009/0299157 A1 * | 12/2009 | Telfort | A61B 5/14551 600/301 |
| 2009/0301754 A1 * | 12/2009 | Morley-Smith | H01B 7/40 174/113 R |
| 2010/0305447 A1 | 12/2010 | Dudik et al. | |
| 2011/0306960 A1 * | 12/2011 | Eisele | A61B 18/1206 606/33 |
| 2015/0229070 A1 * | 8/2015 | Van Swearingen | H01R 13/15 439/320 |
| 2016/0066483 A1 * | 3/2016 | Fukuda | H01B 1/02 174/68.3 |
| 2018/0358739 A1 * | 12/2018 | De Dios Mart N . | H01R 13/447 |

FOREIGN PATENT DOCUMENTS

| | | | |
|---|---|---|---|
| EP | 1112720 A1 * | 7/2001 | ........ A61B 18/1492 |
| JP | H0975365 | 3/1997 | |

* cited by examiner

CABLE CONNECTION SYSTEMS FOR ELECTROSURGICAL SYSTEMS

BACKGROUND

This application claims priority to and the benefit of United State Provisional Patent Application No. 62/351,822, filed Jun. 17, 2016, and entitled CABLE CONNECTION SYSTEMS FOR ELECTROSURGICAL SYSTEMS, the entirety of which in incorporated herein.

1. TECHNICAL FIELD

The present disclosure relates generally to electrosurgical systems. In particular, the present disclosure relates to cable connection systems that enable an electrosurgical return electrode to be connected to multiple wave generators or Electro-Surgical Units.

2. THE RELEVANT TECHNOLOGY

In the area of electrosurgery, medical procedures of cutting tissue and/or cauterizing leaking blood vessels are performed by utilizing radio frequency (RF) electrical energy. As is known to those skilled in the medical arts, electrosurgery is widely used and offers many advantages including the use of a single surgical tool for both cutting and coagulation. The RF energy is produced by wave generators or Electro-Surgical Units (referred to hereinafter as "ESU") and transmitted to a patient's tissue through a hand-held instrument that is operated by a surgeon and that includes an active electrode.

Monopolar electrosurgical generator systems have an active electrode that is applied by the surgeon to the patient at the surgical site to perform surgery and a return path from the patient back to the ESU. The return path includes a return electrode and a cable connected to the ESU for returning the electrosurgical current back to the ESU. In an effort to improve the level of safety during electrosurgical procedures, return electrodes have evolved over the years, from flat stainless steel plates, to relatively small single use flexible return electrodes with adhesive coatings (also known as "sticky pads"), and most recently to relatively large, reusable, self-limiting capacitive or resistive return electrode pads ("self-limiting pads").

While the use of self-limiting return electrodes has dramatically reduced the number of patient burns experienced during electro surgical procedures compared to steel plate and sticky pad return electrodes, there are still challenges encountered during some electrosurgical procedures. For instance, it can be advantageous during some surgical procedures to have multiple surgeons operating on the same patient simultaneously. In such cases, each surgeon uses his or her own active electrode, each of which is connected to a separate ESU. Each ESU also needs to be connected to a return electrode in order to make a complete circuit (e.g., ESU to active electrode to patient to return electrode and back to ESU) so that the electrosurgical current produced by the ESU and delivered to the patient by the active electrode can be returned to the ESU.

Because many, if not most, typical return electrodes include only one ESU connection, one option for allowing multiple surgeons to operate simultaneously on a patient is to use multiple return electrodes to create multiple electrosurgical circuits, one employed by each surgeon. For instance, a first surgeon may use a first electrosurgical circuit that includes a first ESU connected to a first active electrode and a first return electrode. Electrosurgical current produced by the first ESU can be communicated to the patient via the first active electrode and returned to the first ESU via the first return electrode. A second surgeon operating on the same patient may use a second electrosurgical circuit that includes a second ESU connected to a second active electrode and a second return electrode. Electrosurgical current produced by the second ESU can be communicated to the patient via the second active electrode and returned to the second ESU via the second return electrode.

Using multiple return electrodes to create multiple electrosurgical circuits may be accomplished with sticky pads. Due to the many limitations regarding where sticky pads can be placed on a patient, however, actually creating multiple electrosurgical circuits with sticky pads in a safe manner can be quite challenging. Additionally, sticky pads in general do not provide the same level of safety as self-limiting pads.

Although self-limiting pads can provide a higher level of safety than sticky pads, creating multiple electrosurgical circuits when using self-limiting pads can be more difficult than with sticky pads. Due to their relatively large size, it can be challenging to position a patient on multiple self-limiting pads in a way that creates sufficient contact between the patient and both pads. Accordingly, some self-limiting pads have been provided with multiple ESU connections so that a single self-limiting pad can be used simultaneously to create multiple electrosurgical circuits. In other words, the self-limiting pad can be simultaneously connected to multiple ESUs so that electrosurgical current from each ESU can be returned to the ESUs via the same self-limiting pad. The placement of the multiple ESU connections on the self-limiting pads can, however, make it difficult to connect the pad to at least one of the ESUs. For instance, the ESU connections may be located on opposite sides or ends of the pad and the connection cords may not be long enough to reach both ESUs.

Therefore, there are various shortcomings in the present electrosurgical art that can be addressed by embodiments of the present disclosure.

BRIEF SUMMARY

The present disclosure addresses at least some of the foregoing shortcomings by providing cable connection systems that enable a self-limiting electrosurgical return electrode to be simultaneously connected to multiple ESUs. Some embodiments of the disclosed cable connection systems can be used with new or existing self-limiting return electrodes, whether those electrodes have a single built-in ESU connection or multiple built-in ESU connections. Some of the disclosed cable connection systems can be at least partially incorporated into the return electrodes.

In accordance with some embodiments, a cable connection system includes a first return cable, a second return cable, and a junction. The first return cable can provide at least a portion of an electrical path between a return electrode and a first ESU. Similarly, the second return cable can provide at least a portion of an electrical path between the return electrode and a second ESU. The first and second return cables can converge, connect, or be otherwise operatively associated with one another at the junction. The junction can be configured to divide electrosurgical current communicated from the return electrode such that a first portion of the electrosurgical current is communicated to the first ESU and a second portion of the electrosurgical current is communicated to the second ESU.

According to other exemplary embodiments, a cable connection system enables selective connection between an electrosurgical return electrode and multiple ESUs simultaneously. The cable connection system can include a common return cable that is connectable to the return electrode. The common return cable can provide at least a portion of an electrical path between the return electrode and first and second ESUs. A junction can be connectable to the common return cable and the junction can provide at least a portion of the electrical path between the return electrode and the first and second ESUs. A first return cable is connectable between the junction and the first ESU. Similarly, a second return cable is connectable between the junction and the second ESU. The first return cable can provide at least a portion of the electrical path between the return electrode and the first ESU Likewise, the second return cable can provide at least a portion of the electrical path between the return electrode and the second ESU. The junction can divide electrosurgical current communicated from the return electrode such that a first portion of the electrosurgical current is communicated to the first ESU via the first return cable and a second portion of the electrosurgical current is communicated to the second ESU via the second return cable.

In other exemplary embodiments, a cable connection system includes first and second return cables that can provide at least portions of electrical paths between the return electrode and respective first and second ESUs. The first return cable can include a connector at a distal end that is selectively connectable to the first ESU. Similarly, the second return cable can include a connector at a distal end that is selectively connectable to the second ESU. The proximal ends of the first and second return cables can include a shared common connector. The first and second return cables can be selectively connectable to a single connector associated with the return electrode via the shared common connector.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

Additional features and advantages of the disclosed embodiments will be set forth in the description which follows, and in part will be obvious from the description, or may be learned by the practice of the disclosure. These and other features will become more fully apparent from the following description and appended claims, or may be learned by the practice of the present disclosure.

BRIEF DESCRIPTION OF THE DRAWINGS

To further clarify the above and other advantages and features of the present disclosure, a more particular description will be rendered by reference to specific embodiments thereof which are illustrated in the appended drawings. It is appreciated that these drawings depict only illustrated embodiments of the disclosure and are therefore not to be considered limiting of its scope. The disclosure will be described and explained with additional specificity and detail through the use of the accompanying drawings in which.

DETAILED DESCRIPTION

The present disclosure relates to cable connection systems for simultaneously connecting an electrosurgical return electrode to multiple ESUs. Some embodiments of the disclosed cable connection systems can be used with new or existing self-limiting return electrodes, whether those electrodes have a single built-in ESU connection or multiple built-in ESU connections. Some of the disclosed cable connection systems can be at least partially incorporated into the return electrodes.

Reference will now be made to the drawings to describe various aspects of exemplary embodiments. It is understood that the drawings are diagrammatic and schematic representations of such exemplary embodiments, and are not limiting of the claimed subject matter, nor are any particular elements to be considered essential for all embodiments or that elements be assembled or manufactured in any particular order or manner. No inference should therefore be drawn from the drawings as to the necessity of any element.

In the following description, numerous specific details are set forth in order to provide a thorough understanding of the presently disclosed embodiments. It will be obvious to one of ordinary skill in the art, however, that the presently disclosed embodiments may be practiced without these specific details. In other cases, well known aspects of electrosurgical systems, devices, and methods, and general manufacturing techniques are not described in detail herein in order to avoid unnecessarily obscuring the novel aspects of the presently disclosed embodiments.

Figure 1:
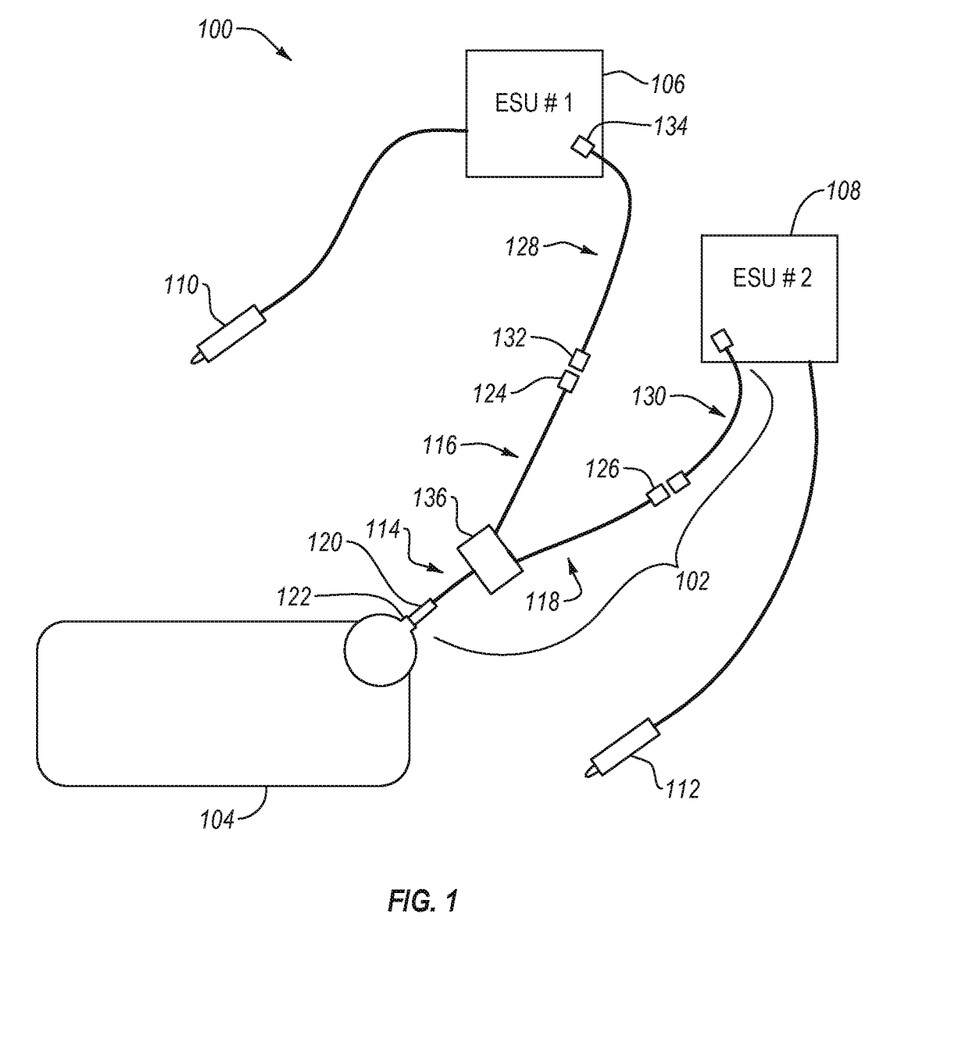
FIG. 1 illustrates an electrosurgical system incorporating a cable connection system according to an example embodiment of the present disclosure.

FIG. 1 illustrates an electrosurgical system 100 that employs or includes one example embodiment of a cable connection system 102 that enables a return electrode 104 to be simultaneously connected to multiple ESUs, such as first ESU 106 and second ESU 108. Although the cable connection system 102 of FIG. 1 (as well as the other disclosed embodiments) is described and illustrated as allowing for connection to two ESUs, it will be appreciated that this arrangement is merely exemplary. Cable connection systems according to the present disclosure may allow for a return electrode to be simultaneously connected to more than two ESUs.

Simultaneously connecting the return electrode 104 to multiple ESUs (e.g., the first and second ESUs 106, 108) allows multiple active electrodes, such as first electrode 110 and second electrode 112, to be used simultaneously on a patient during an electrosurgical procedure. For instance, a patient may be positioned on the return electrode 104 during an electrosurgical procedure. A first surgeon may use the first electrode 110 and a second surgeon may use the second electrode 112 to perform the electrosurgical procedure on the patient.

Upon activation of the first electrode 110, the first ESU 106 produces and transmits electrosurgical current to the first electrode 110, which is applied to the patient to effectuate cutting or cauterization. The electrosurgical current is returned to the first ESU 106 via the return electrode 104 and the cable connection system 102. Similarly, upon activation of the second electrode 112, the second ESU 108 produces and transmits electrosurgical current to the second electrode 112, which is applied to the patient to effectuate cutting or cauterization. The electrosurgical current is returned to the second ESU 108 via the return electrode 104 and the cable connection system 102. In this way multiple surgeons can operate on a patient at the same time and the electrosurgical current can be returned to its originating ESU (thereby completing the electrosurgical circuit).

In the embodiment illustrated in FIG. 1, the cable connection system 102 includes a return electrode connection cable 114 (also referred to herein as common return cable 114), a first return connection cable 116 (also referred to herein as first return cable 116), and a second return connection cable 118 (also referred to herein as second return cable 118). Each of the noted cables includes a connector for connection to an associated component of the electrosurgical system 100 and/or the cable connection system 102. For instance, the common return cable 114 includes a connector 120 that is designed to selectively, semi-permanently, or permanently connect the common return cable 114 to a connector 122 on the return electrode 104. The connection between the connectors 120, 122 allows for the electrosurgical current to pass from the return electrode 104 into the cable connection system 102.

Similar to connector 120, the first and second return cables 116, 118 include respective connectors 124, 126. The connectors 124, 126 may be designed to connect the first and second return cables 116, 118 directly or indirectly to respective ESUs (e.g., the first and second ESUs 106, 108). For instance, the connector 124 may be specifically designed for connection to the first ESU 106 and the connector 126 may be specifically designed for connection to the second ESU 108. In other embodiments, the connectors 124, 126 may be designed to be interchangeably connected to either of the first and second ESUs 106, 108. Thus, the connectors 124, 126 may have similar or dissimilar designs.

As noted, the connectors 124, 126 may allow for the first and/or second return cables 116, 118 to be indirectly connected to the first and/or second ESUs 106, 108. For instance, as illustrated in FIG. 1, the cable connection system 102 may include one or more ESU adaptor cables 128, 130. The ESU adaptor cables 128, 130 may be used as extension cables for the first and second return cables 116, 118. Thus, if the common return cable 114, the first return cable 116, and/or the second return cable 118 is/are not long enough to allow for the return electrode 104 to be connected to the first and/or second ESUs 106, 108, one or both of the adaptor cables 128, 130 may be used to connect the first and/or second return cables 116, 118 to the first and/or second ESUs 106, 108.

The ESU adaptor cables 128, 130 may also allow for connections between the first and second return cables 116, 118 and otherwise incompatible ESUs. For instance, the first ESU 106 may include a connector that is not designed to accept, connect to, or otherwise mate with the connector 124. The ESU adaptor cable 128 may include a connector 132 that is compatible with (e.g., designed to accept, connect to, or otherwise mate with) the connector 124. The ESU adaptor cable 128 may also include a connector 134 that is compatible with the first ESU 106. Thus, the ESU adaptor cable 128 may allow for the first return cable 116 to be connected to the first ESU 106 even when the first return cable 116 and the first ESU 106 have otherwise incompatible connectors. Similarly, the ESU adaptor cable 130 may include connectors that allow for the second return cable 118 to be connected to the second ESU 108 even when the second return cable 118 and the second ESU 108 have otherwise incompatible connectors.

In the illustrated embodiment, the common return cable 114, the first return cable 116, and the second return cable 118 converge, connect, and/or are otherwise associated with one another at junction 136. The junction 136 and/or the connection or association of the cables 114, 116, 118 therein may take a variety of forms. For instance, the junction 136 may be a housing in which the ends of the cables 114, 116, 118 are electrically connected together. In some embodiments, two of the identified cables 114, 116, 118 may actually be formed of a single cable and the third cable may be connected thereto. By way of example, the common return cable 114 and the first return cable 116 may be part of a single cable. In such an embodiment, the second return cable 118 may be connected to the single cable at the junction 136. Regardless of the specific configuration of the junction 136, the junction 136 can provide at least a portion of the electrical path between the return electrode 104 and the first and second ESUs 106, 108. Additionally, the electrosurgical current communicated from the return electrode 104 can be divided at or by the junction 136 such that a first portion of the electrosurgical current is communicated to the first ESU 106 and a second portion of the electrosurgical current is communicated to the second ESU 108.

Figure 2:
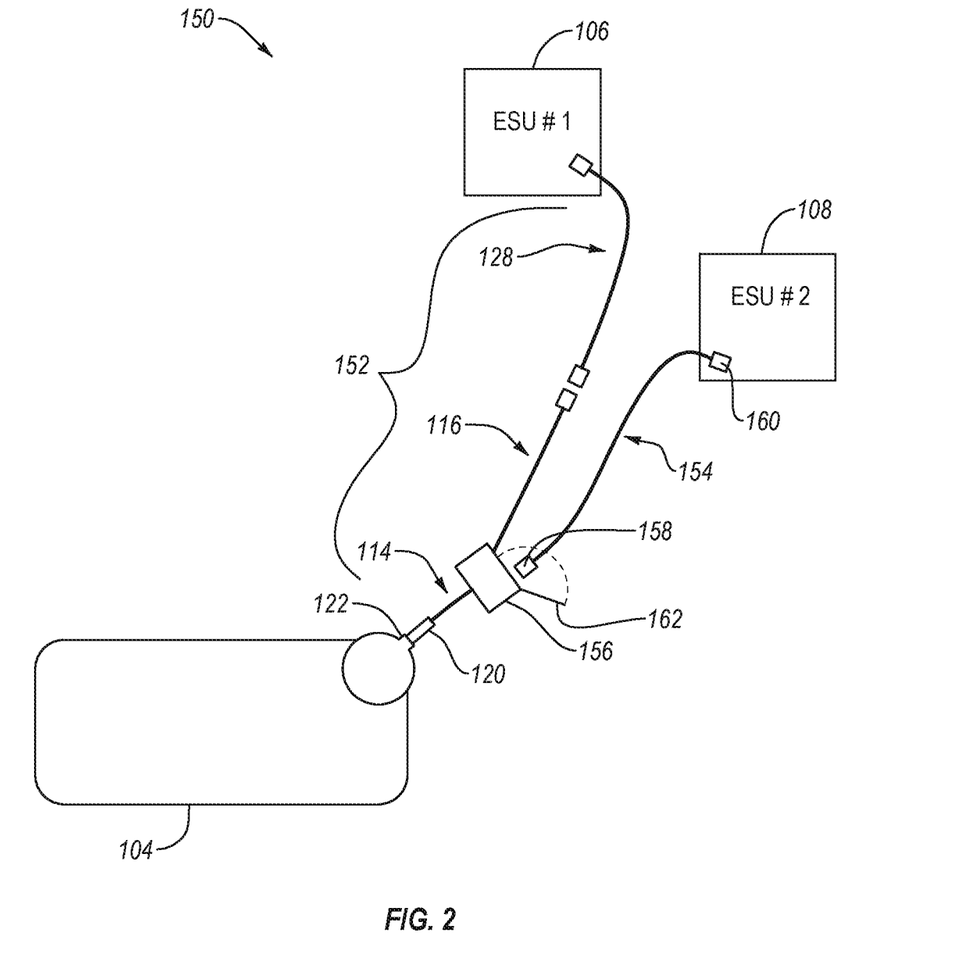
FIG. 2 illustrates an electrosurgical system incorporating a cable connection system according to another example embodiment of the present disclosure.

Attention is now directed to FIG. 2, which illustrated another electrosurgical system 150. As can be seen, electrosurgical system 150 includes many elements that are similar or identical to those of electrosurgical system 100. Accordingly, in describing the embodiment of FIG. 2, attention will be focused on the aspects of electrosurgical system 150 that are unique from those of electrosurgical system 100.

Electrosurgical system 150 includes a cable connection system 152 for connecting the return electrode 104 to multiple ESUs (e.g., the first and second ESUs 106, 108). The cable connection system 152 includes a common return cable 114, a first return cable 116, and an ESU adaptor cable 128 that may be similar or identical to those described above in connection with FIG. 1.

The cable connection system 152 also includes a second return cable 154 and a junction 156. In the illustrated embodiment, the second return cable 154 may be selectively connected to and disconnected from the junction 156. More specifically, the second return cable 154 includes a connector 158 that is designed to be connected to a connector (not shown) of the junction 156. When the second return cable 154 is disconnected from the junction 156, the cable connection system 152 allows for the return electrode 104 to be singly connected to the first ESU 106. In contrast, when the second return cable 154 is connected to the junction 156, the cable connection system 152 allows for the return electrode 104 to be connected to both of the first and second ESUs 106, 108. To facilitate the connection of the second return cable 154 to the second ESU 108, the second return cable 154 also includes a connector 160 that is designed for connection to at least the second ESU 108.

In addition to allowing for selective connection and disconnection of the second return cable 154, the junction 156 illustrated in FIG. 2 also includes a cover 162. The cover 162 may be selectively opened to provide access to the junction connector to allow the second return cable 154 to be connected to the junction 156. When the second return cable 154 is disconnected from the junction, the cover 162 may be closed to cover the junction connector. Covering the junction connector when not in use may provide various benefits, such as preventing contaminates, fluids, and the like from entering the junction connector.

Although FIG. 2 only illustrates the second return cable 154 being selectively connectable to the junction 156, it will be appreciated that the first return cable 116 and/or one or more additional return cables may be selectively connectable to the junction 156. For instance, the junction 156 may include one or more junction connectors that allow for one or more return cables to be selectively connected to the junction. The one or more junction connectors may be associated with one or more covers that selectively cover one or more of the junction connectors when not in use.

Figure 3A:
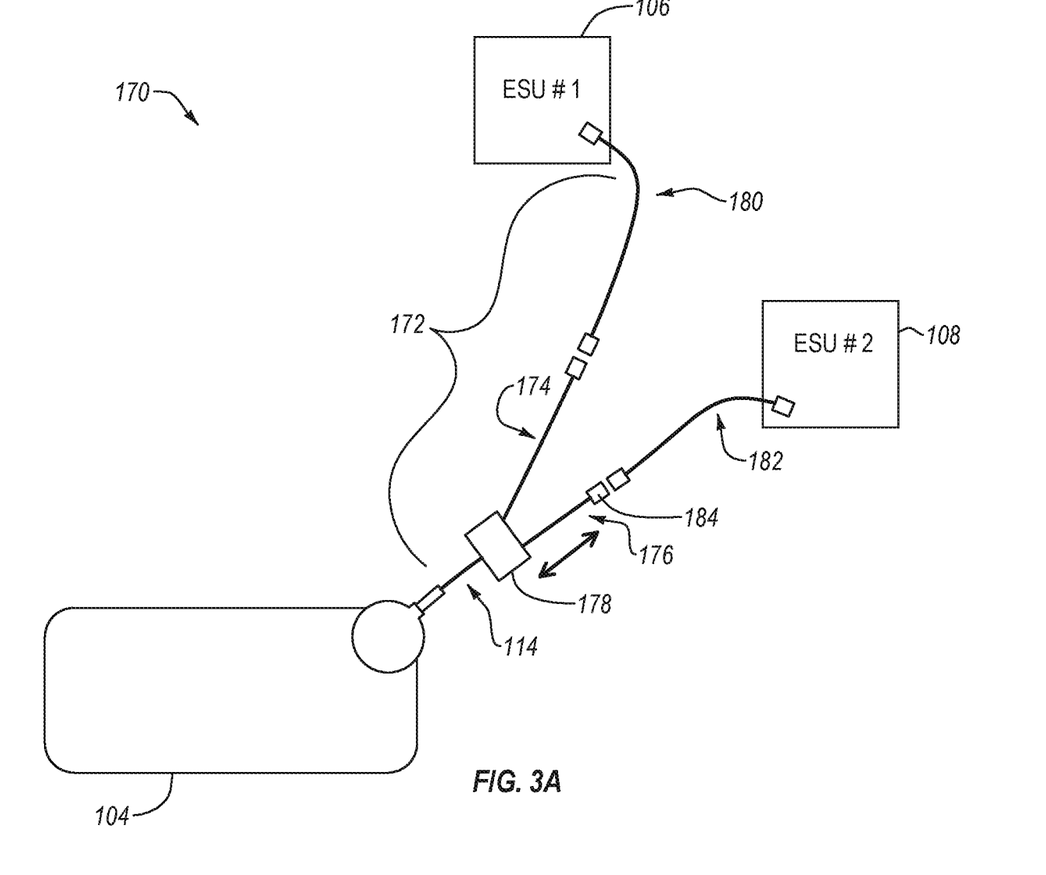
FIG. 3A illustrates an electrosurgical system incorporating a cable connection system according to yet another example embodiment of the present disclosure.
Figure 3B:
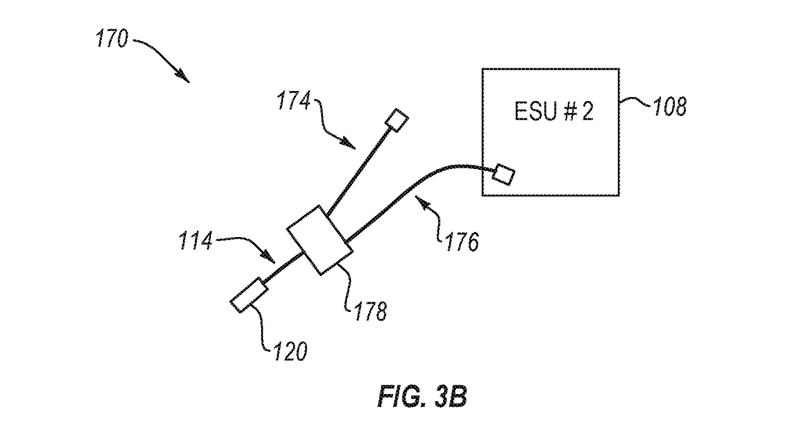
FIG. 3B illustrates a portion of an electrosurgical system incorporating the cable connection system of FIG. 3A as used in a different manner.

Turning now to FIGS. 3A and 3B, illustrated is a cable connection system with one or more selectively extendable and retractable cables. The selectively extendable nature of the cable(s) may allow for the length of the cable(s) to be selectively adjusted as desired for a particular procedure or operating room arrangement, such that, for example, additional adaptor cables are not needed. Similarly, the selectively retractable nature of the cable(s) may allow for the cable(s) to be selectively retracted into a storage position when the cable(s) and/or the cable connection system is not in use.

For instance, FIGS. 3A and 3B illustrate an electrosurgical system 170 that is similar to the electrosurgical system 100 of FIG. 1. In particular, the electrosurgical system 100 includes a cable connection system 172 for connecting the return electrode 104 to multiple ESUs (e.g., the first and second ESUs 106, 108). Similar to cable connection system 102, cable connection system 172 includes a common return cable 114, first and second return cables 174, 176, a junction 178, and optional ESU adaptor cables 180, 182.

According to the present embodiment, one or more of the cables 114, 174, 176 may be selectively extendable from and retractable to/into the junction 178. For instance, the two-headed arrow in FIG. 3A illustrates that the second return cable 176 is selectively extendable from and retractable to/into the junction 178. Thus, for example, when the second return cable 176 is not being used (e.g., when the cable connection system 172 is not in use or when the cable connection system 172 is used only to connect the return electrode 104 to the first ESU 106), the second return cable 176 may be retracted to/into the junction 178.

To facilitate the extension/retraction of the second return cable 176, the junction 178 may be equipped with a winding device. The winding device may include a spool on which the second return cable 176 may be wound. In some embodiments, the winding device may be manually operated via a crank that is accessible from the outside of the junction 178. In other embodiments, the winding device may be a spring-loaded device that automatically retracts the second return cable 176 upon activation of the spring-loaded device (e.g., release of a lock/brake mechanism, short pull on the second return cable 176, etc.).

To extend the second return cable 176 from the junction 178, the second return cable 176 may be pulled out of the junction 178 so that the second return cable 176 is at least partially unwound from the spool of the winding device. A lock/brake mechanism may selectively retain the second return cable 176 at a desired length and until the second return cable 176 is either extended further out of the junction 178 or until the winding device is activated to retract the second return cable 176.

When the second return cable 176 is completely retracted, the second return cable 176 may fit entirely within the junction 178. In some such embodiments, the junction 178 may include a cover (e.g., similar to cover 162) to close off the compartment in the junction 178 in which the second return cable 176 is disposed. In other embodiments, the second return cable 176 may not be entirely disposed within the junction 178 when the second return cable 176 is completely retracted. For instance, the connector 184 may be disposed on the outside of the junction 178, which may facilitate extension of the second return cable 176 when desired.

The selectively extendable/retractable nature of the cable(s) may allow the length(s) of the cable(s) to be adjusted relative to one another. For instance, FIG. 3A illustrates the second return cable 176 extended out of the junction 178 to a length that is shorter than the length of the first return cable 174. In contrast, FIG. 3B illustrates the second return cable 176 extended out of the junction 178 to a length that is longer than the length of the first return cable 174. The selectively extendable nature of the cable(s) may also allow the cable(s) to be connected directly to the ESUs without additional adaptor cables. For instance, as shown in FIG. 3B, the second return cable 176 is extended out of the junction 178 far enough to reach the second ESU 108. In contrast, FIG. 3A illustrates the adaptor cable 182 facilitating the connection between the second return cable 176 and the second ESU 108.

Although FIGS. 3A and 3B and the related description have focused on the second return cable 176 being selectively extendable/retractable, it will be understood that any one or more of the cables associated with the junction 178 may be selectively extendable/retractable. For instance, the first return cable 174 may be selectively extendable/retractable in addition to or as an alternative to the second return cable 176. Likewise, the common return cable 114 may be selectively extendable/retractable regardless of whether one or both of the first and second return cables 174, 176 are selectively extendable/retractable.

Figure 4:
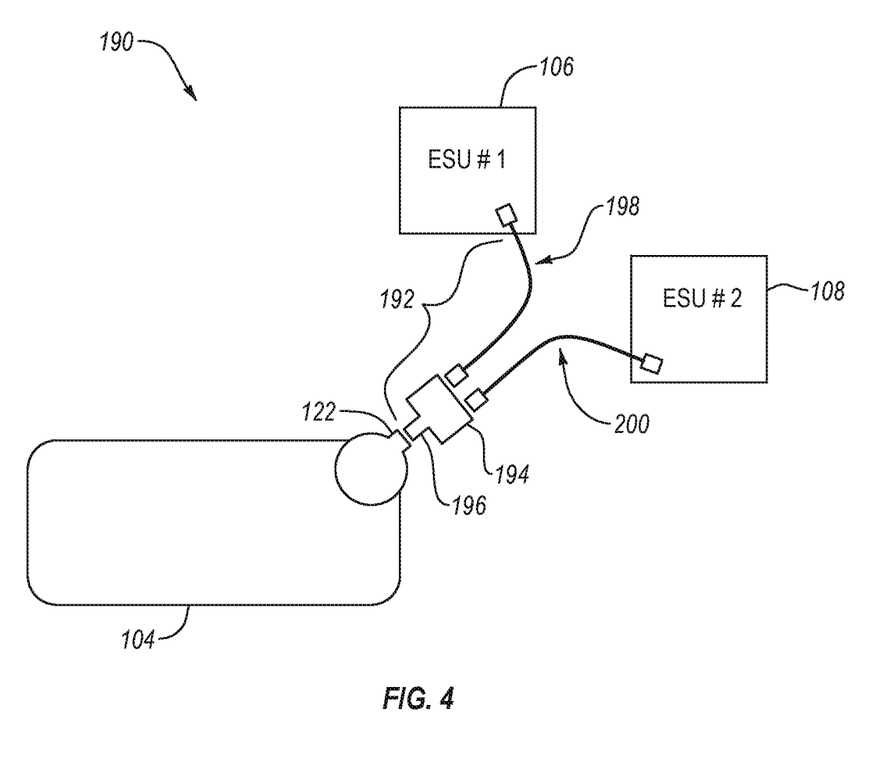
FIG. 4 illustrates an electrosurgical system incorporating a cable connection system according to still another example embodiment of the present disclosure.

Attention is now directed to FIG. 4, which illustrates an electrosurgical system 190 having a cable connection system 192 for connecting the return electrode 104 to multiple ESUs (e.g., the first and second ESUs 106, 108). Unlike the previously described cable connection systems, the cable connection system 192 does not have a common return cable. Rather, the cable connection system 192 includes a junction 194 that is directly connectable to the return electrode 104.

In the illustrated embodiment, the junction 194 includes a connector 196 that can be connected to the connector 122 on the return electrode 104. The connection between the connector 196 and the connector 122 may be designed for selective connection and disconnection. In other embodiments, the connection may be a more permanent connection such that once the connector 196 is connected to the connector 122 the connector 196 cannot be disconnected therefrom. In still other embodiments, the connection may be a semi-permanent connection. That is, the connector 196 may be disconnected from the connector 122, but the disconnection may be more difficult that disconnecting other connectors in the system 190.

The cable connection system 192 also includes a first return cable 198 and a second return cable 200. In the illustrated embodiment, the first return cable 198 is selectively connectable to and disconnectable from the junction 194 and the first ESU 106. Similarly, the second return cable 200 is selectively connectable to and disconnectable from the junction 194 and the second ESU 108. More specifically, the first and second return cables 198, 200 include connectors that allow for connections to be made with the junction 194 and the first and second ESUs 106, 108. In some embodiments, the first and second return cables 198, 200 may have similar or identical connectors such that the first and second return cables 198, 200 are interchangeable. In other embodiments, the first and second return cables 198, 200 may have one or more dissimilar connectors, so as to, for example, facilitate connections to different types of ESUs Although FIG. 4 illustrates the first and second return cables 198, 200 as being selectively connectable to the junction 194, it will be appreciated that one or both of the first and second return cables 198, 200 may be more permanently connected to the junction 194, similar to the embodiments illustrated in FIGS. 1-3B. Additionally, one or both of the first and second return cables 198, 200 may be selectively extendable from and retractable to/into the junction 194 as described elsewhere herein.

Figure 5:
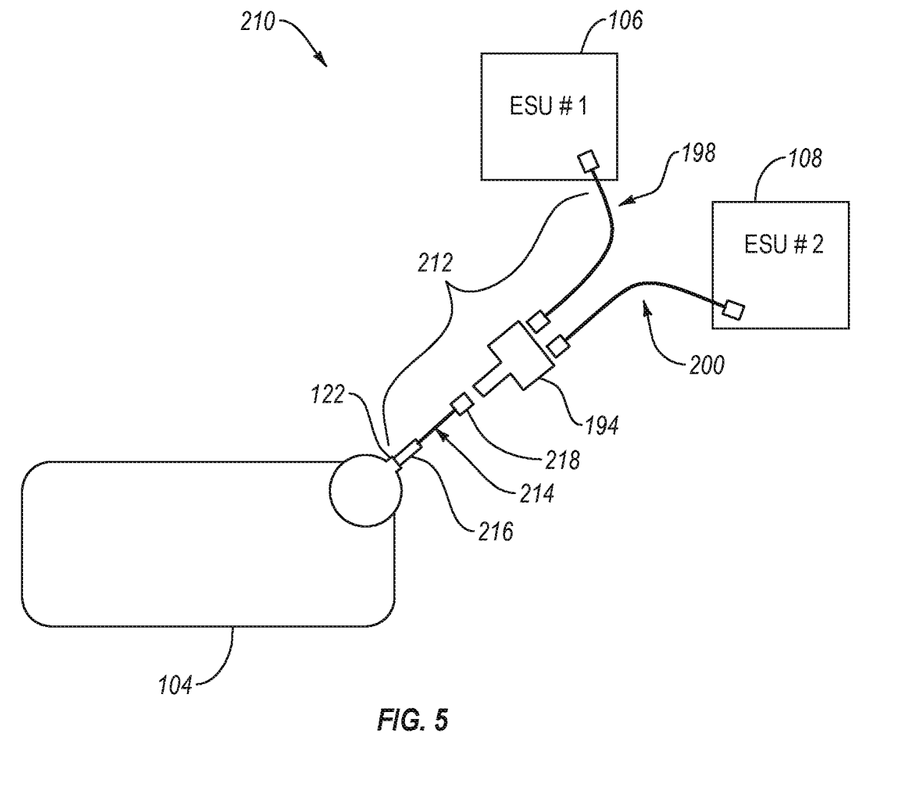
FIG. 5 illustrates an electrosurgical system incorporating a cable connection system according to yet still another example embodiment of the present disclosure.

FIG. 5 illustrates an electrosurgical system 210 that includes a cable connection system 212 that is similar in many respects to cable connection system 192 illustrated in FIG. 4. One distinguishing feature of cable connection system 212 compared to cable connection system 192 is the inclusion of a common return cable 214 in cable connection system 212. In some embodiments, common return cable 214 may be designed to allow for selective connection between the return electrode 104 and the junction 194.

More specifically, the common return cable 214 may include a connector 216 designed for connection to the connector 122 on the return electrode 104. The common return cable 214 also includes a connector 218 designed for connection to the junction 194. In some embodiments, the connectors 216, 218 may be dissimilar connectors. Such configuration may allow for the return electrode 104 to be connected to the junction 194 even when the connector 122 and the junction connector are not designed to be connected together. In other words, the common return cable 214 may function as an adaptor cable.

Figure 6:
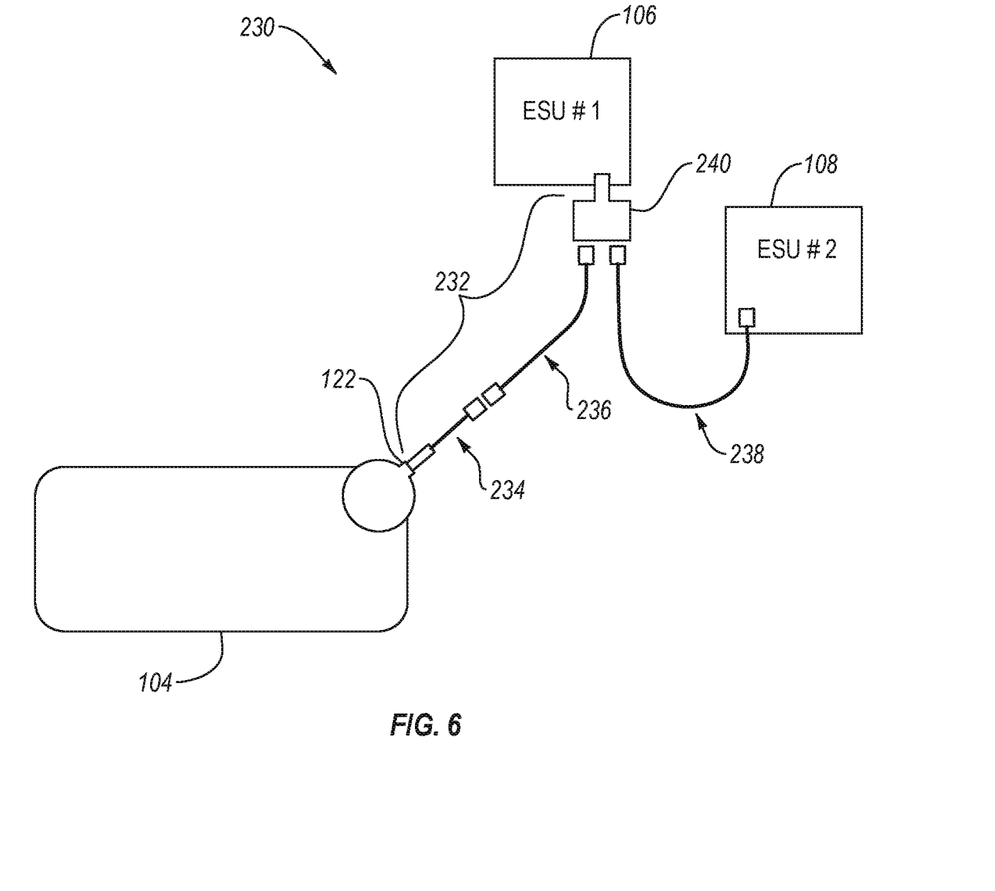
FIG. 6 illustrates an electrosurgical system incorporating a cable connection system according to a further example embodiment of the present disclosure.

FIG. 6 illustrates another electrosurgical system 230 that includes a cable connection system 232 for connecting the return electrode 104 to multiple ESUs (e.g., the first and second ESUs 106, 108). The cable connection system 232 includes a common return cable 234, a first return cable 236, a second return cable 238, and a junction 240. Unlike the previous embodiments that include a common return cable, the common return cable 234 of the present embodiment connects to the first return cable 236 rather than the junction 240. The opposing end of the first return cable 236 connects to the junction 240, which in turn connects to the first ESU 106. The second return cable 238 is connected between the junction 240 and the second ESU 108.

As discussed in connection with the other embodiments herein, the various connections between the components of the electrosurgical system 230 and/or the cable connection system 232 may be selective, semi-permanent, or permanent connections. For instance, the connections between the common return cable 234 and the return electrode 104 and between the junction 240 and the first ESU 106 may be permanent or semi-permanent connections, while the connections between the common return cable 234 and the first return cable 236, between the junction 240 and the first and second return cable 236, 238, and between the second return cable 238 and the second ESU 108 may be selective connections.

Figure 7:
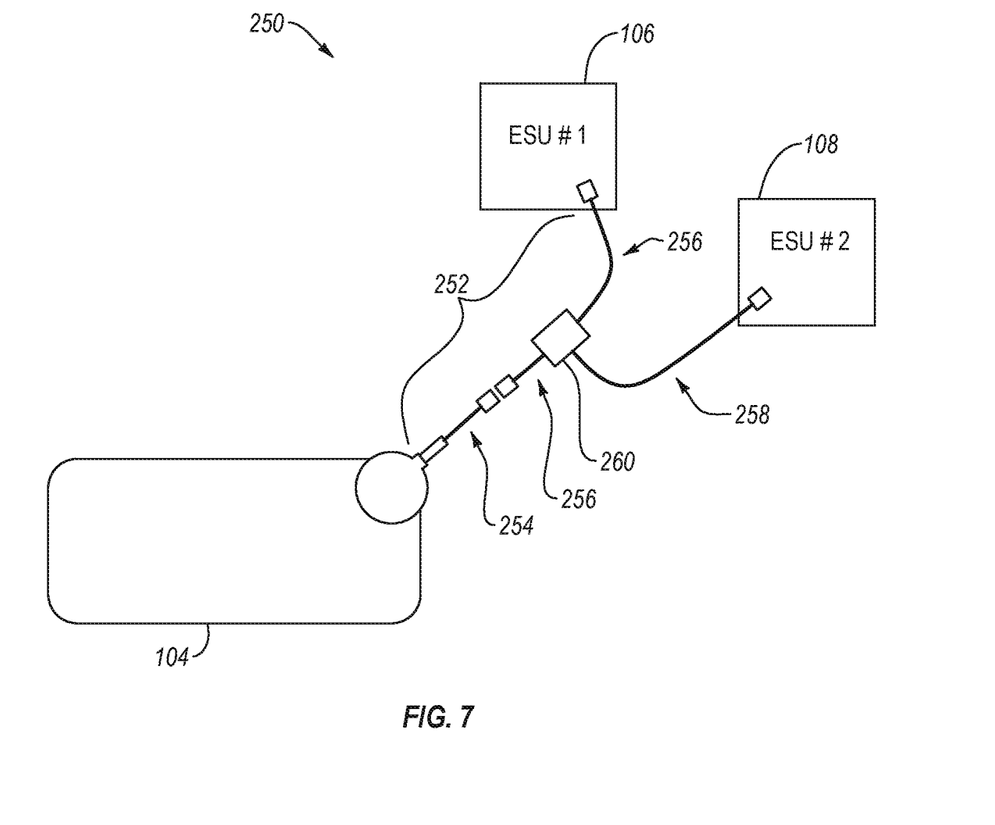
FIG. 7 illustrates an electrosurgical system incorporating a cable connection system according to another example embodiment of the present disclosure.

Attention is now directed to FIG. 7, which illustrates an electrosurgical system 250 that includes a cable connection system 252 that allows for the return electrode 104 to be connected to multiple ESUs (e.g., the first and second ESUs 106, 108). According to FIG. 7, the cable connection system 252 includes an optional common return cable 254 that can be selectively, semi-permanently, or permanently connected to the return electrode 104. The cable connection system 252 also includes a first return cable 256 that is connected between the common return cable 254 (or the return electrode 104 if the common return cable 254 is omitted) and the first ESU 106.

The cable connection system 252 also include a second return cable 258 and junction 260. The junction 260 may be selectively connected to the first return cable 256 or the common return cable 254 when the return electrode 104 needs to be connected to the second ESU 108. The junction 260 may include a coupling connector that connects the second return cable 258 to either the first return cable 256 or the common return cable 254. For instance, the coupling connector may include or take the form of a clamp feature that physically connects the junction 260 to the first return cable 256 or the common return cable 254.

Although the junction 260 may physically connect the second return cable 258 to the first return cable 256 or the common return cable 254, the connection may not create a direct conductive electrical connection between the second return cable 258 and either the first return cable 256 or the common return cable 254. Rather, for instance, the junction 260 may create a capacitive connection between the second return cable 258 and either the first return cable 256 or the common return cable 254. More specifically, the first return cable 256 and/or the common return cable 254 may include a conductive core and an insulative outer sheath. When the junction 260 is connected to either the first return cable 256 or the common return cable 254, a conductive element in the junction 260 and/or the second return cable 258 may be positioned close enough to the first return cable 256 or the common return cable 254 to create a capacitive connection therebetween. As a result, at least some of the electrosurgical current passed from the return electrode may be communicated from the first return cable 256 or the common return cable 254 to the junction 260 and/or the second return cable 258 via a capacitive connection therebetween.

At least a portion of an insulative outer sheath of the first return cable 256 and/or the common return cable 254 may be configured to facilitate the capacitive connection between the junction 260 and the first return cable 256 or the common return cable 254. For instance, a portion of the outer insulative sheath may be thinner and/or have a different dielectric constant than other portions of the insulative outer sheath in order to facilitate a stronger capacitive connection.

Figure 8:
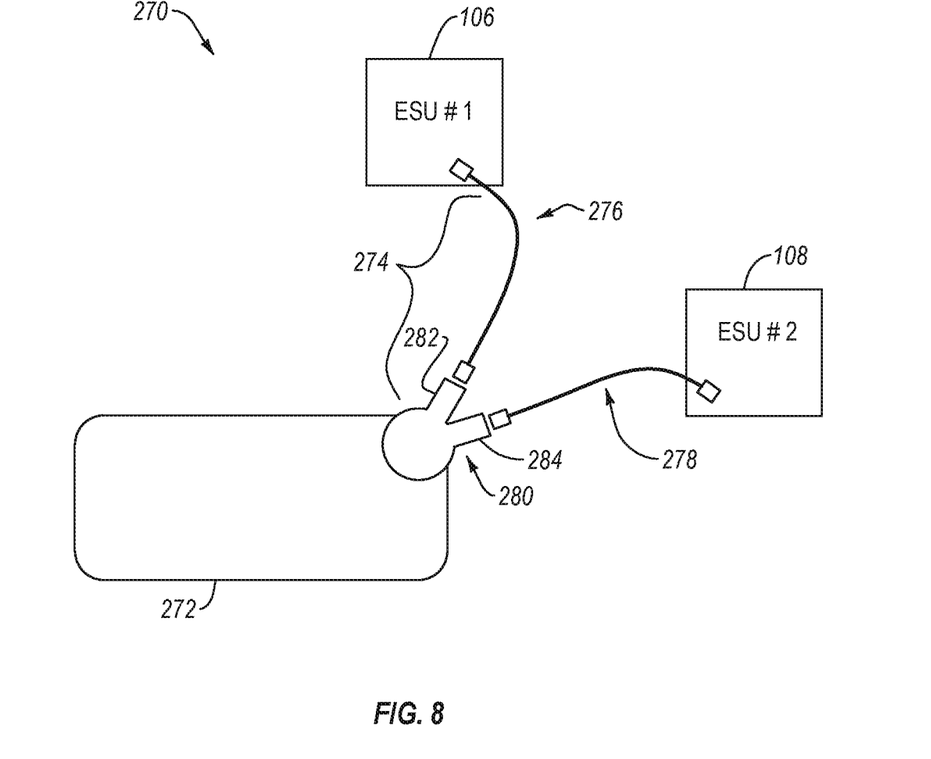
FIG. 8 illustrates an electrosurgical system incorporating a cable connection system according to another example embodiment of the present disclosure.

Turning now to FIG. 8, there is illustrated an electrosurgical system 270 that includes a return electrode 272 that can be connected to multiple ESUs (e.g., the first and second ESUs 106, 108) via a cable connection system 274. Similar to some of the other cable connection systems disclosed herein, the cable connection system 274 includes first and second return cables 276, 278. The first and second return cables 276, 278 may be selectively connected to the first and second ESUs 106, 108.

Unlike some of the other cable connection systems described herein, the cable connection system 274 does not have a separate and distinct junction. Rather, the cable connection system 274 includes a junction 280 integrated with the return electrode 272. Similar to some of the other junctions described herein, the junction 280 includes at least two connectors 282, 284 to which the first and second return cables 276, 278 may be connected. As illustrated in FIG. 8, the connectors 282, 284 may be disposed at the same corner (or other location) of the return electrode 272. The connectors 282, 284 may share or be incorporated into a single junction housing, such as an overmold. In any case, the junction 280 may be designed to allow electrosurgical current to pass from the return electrode 272 to both of the first and second return cables 276, 278.

Figure 9:
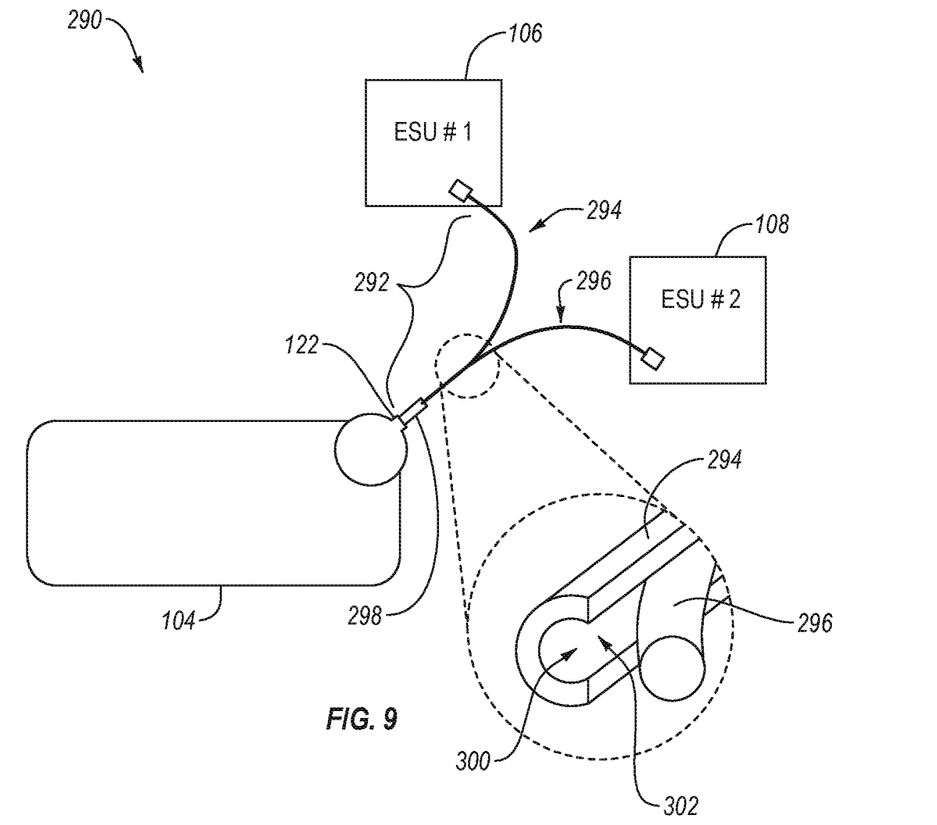
FIG. 9 illustrates an electrosurgical system incorporating a cable connection system according to an example embodiment of the present disclosure.

Attention is now directed to FIG. 9, which illustrates an electrosurgical system 290 that includes a cable connection system 292 that allows for the return electrode 104 to be connected to multiple ESUs (e.g., the first and second ESUs 106, 108). The cable connection system 292 includes a first return cable 294 and a second return cable 296. The ends of the first and second return cables 294, 296 near the return electrode 104 share or are joined together at a common connector 298. The connector 298 is designed to be connected to the return electrode 104 at the connector 122. The opposing ends of the first and second return cables 294, 296 may be selectively connected to the first and second ESUs 106, 108.

In addition to sharing a common connector 298, the first and second return cables 294, 296 may also be designed to be joined together along at least a portion of their respective lengths. FIG. 9 includes a close-up partial cutaway view illustrating one example configuration that allows for the first and second return cables 294, 296 to be selectively joined together. In the illustrated embodiment, the first and second return cables 294, 296 may be selectively nested together along at least a portion of their respective lengths.

According to FIG. 9, for instance, the first return cable 294 may have a generally C-shaped cross-section that defines an interior cable retention area 300 and an opening 302 that provides access to the retention area 300. The retention area 300 and the opening 302 may extend along a portion (e.g., 10%, 25%, 35%, 50%, 75%, 90%) of the length of the first return cable 294. The second return cable 296 may include a cross-sectional shape that generally corresponds to the retention area 300. Additionally, the retention area 300, the opening 302, and the second return cable 296 may be sized such that the second return cable 296 may be selectively passed through the opening 302 into and out of the retention area 300. The relative sizes of the opening 302 and the second return cable 296 may be such that the second return cable 296 is retained in the retention area 300 until sufficient force is applied to pull the second return cable 296 out of the first return cable 294. The withdrawal force can be relatively minimal, such that a user can relatively easily pull the first and second return cables 294, 296 apart, but not so minimal that the first and second return cables 294, 296 separate without an intentional force being applied (e.g., by a user).

It will be understood that the present disclosure extends beyond the specific combinations of features illustrated and described in connection with the various particular embodiments disclosed herein. For instance, although a particular embodiment described herein may include a combination of multiple features, the present disclosure extends to embodiments that include one or more of the described features. Additionally, it will be understood that a feature described in connection with one embodiment may be incorporated into another embodiment without departing from the disclosure.

It will now be evident that there have been described herein improved cable connection systems. The disclosed cable connection systems allow for more versatility in electrosurgical procedures. For instance, the cable connection systems allow for a return electrode to be selectively connected to multiple ESU's simultaneously.

The terms "approximately," "about," and "substantially" as used herein represent an amount close to the stated amount that still performs a desired function or achieves a desired result. For example, the terms "approximately," "about," and "substantially" may refer to an amount that is within less than 10% of, within less than 5% of, within less than 1% of, within less than 0.1% of, and within less than 0.01% of a stated amount.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An electrosurgical system for selectively connecting to multiple Electro-Surgical Units (ESUs) simultaneously, the electrosurgical system comprising:
   an electrosurgical return electrode, the electrosurgical return electrode comprising a junction integrally formed therewith, the junction comprising a first connector and a second connector, the junction being configured to divide electrosurgical current into a first portion of the electrosurgical current that is communicated from the electrosurgical return electrode via the first connector and a second portion of the electro surgical current is communicated from the electrosurgical return electrode via the second connector;
   a first return cable connectable between the first connector of the junction and a first ESU, the first return cable being configured to communicate the first portion of the electrosurgical current from the first connector to the first ESU, the first return cable comprising a connector that is configured to be selectively connected to and disconnected from the first ESU; and
   a second return cable connectable between the second connector of the junction and a second ESU, the second return cable being configured to communicate the second portion of the electrosurgical current from the second connector to the second ESU, the second return cable comprising a connector that is configured to be selectively connected to and disconnected from the second ESU.

2. A cable connection system according to claim 1, wherein at least one of the first and second return cables is selectively connectable to and disconnectable from the junction.

3. A cable connection system according to claim 1, wherein the junction further comprises a cover for selectively covering the second connector when the second return cable is disconnected from the second connector.

4. A cable connection system according to claim 1, wherein the first return cable is selectively extendable from and retractable at least partially into the junction.

5. A cable connection system according to claim 4, wherein the junction comprises a winding device that enables the selective extension and retraction of the first return cable.

6. A cable connection system according to claim 4, wherein the junction comprises a cover for selectively covering the first return cable when the first return cable is retracted into the junction.

7. A cable connection system according to claim 1, wherein the connectors of the first and second return cables are not interchangeably connectable to a common ESU connection.

8. A cable connection system according to claim 1, wherein the connectors of the first and second return cables are interchangeably connectable to a common ESU connection.

9. A cable connection system according to claim 1, wherein the junction comprises one or more additional connectors for selective connection with one or more additional return cables.

10. A cable connection system according to claim 1, wherein the first and second connectors of the junction share a single junction housing.

11. A cable connection system according to claim 1, wherein the junction and the first and second connectors thereof are disposed at a corner of the return electrode.

12. A cable connection system according to claim 1, wherein the first and second return cables are selectively joinable together along at least a portion of their respective lengths.

13. A cable connection system according to claim 12, wherein the first return cable comprises an interior retention area extending along at least a portion of its length and which is configured to have the second return cable selectively disposed therein.

14. A cable connection system according to claim 13, wherein the first return cable comprises an opening along at least a portion of its length and through which the second return cable is selectively insertable into or removable from the interior retention area.

15. A cable connection system according to claim 12, wherein at least a portion of the first return cable has a substantially C-shaped cross-section.

16. A cable connection system according to claim 1, further comprising one or more ESU adaptor cables selectively connectable between at least one of the first and second return cables and the first and second ESUs.

17. A cable connection system according to claim 1, wherein at least one of the first and second return cables is selectively connectable to the junction.

18. A cable connection system according to claim 1, wherein at least one of the first and second return cables is selectively extendable from and retractable at least partially into the junction.

19. A cable connection system for selectively connecting an electrosurgical return electrode to multiple Electro-Surgical Units (ESUs) simultaneously, the cable connection system comprising:
  a first return cable that provides at least a portion of an electrical path between the return electrode and a first ESU, the first return cable comprising a first connector at a distal end thereof that is selectively connectable to and disconnectable from the first ESU and a second connector at a proximal end thereof that is selectively connectable to and disconnectable from the return electrode; and
  a second return cable that provides at least a portion of an electrical path between the return electrode and a second ESU, the second return cable comprising a first connector at a distal end thereof that is selectively connectable to and disconnectable from the second ESU and a junction at a proximal end thereof, the junction being integrally formed with the proximal end of the second return cable,
  wherein the junction is selectively connectable to and disconnectable from the first return cable in such a manner as to create a non-conductive, capacitive electrical connection between the first and second return cables, and
  wherein the junction is configured to divide electrosurgical current communicated from the return electrode such that a first portion of the electrosurgical current is communicated to the first ESU via the first return cable and a second portion of the electrosurgical current is communicated to the second ESU via the second return cable.

20. A cable connection system of claim 19, wherein the first return cable comprises a conductive core and an insulative outer sheath, wherein a first portion of the insulative outer sheath has a first thickness or first dielectric constant and a second portion of the insulative outer sheath has a second thickness or second dielectric constant that is different from the first thickness or first dielectric constant, wherein the difference between the first thickness or the first dielectric constant and the second thickness or the second dielectric constant facilitates the non-conductive, capacitive electrical connection between the first and second return cables.

21. A cable connection system according to claim 19, wherein a portion of the first return cable functions as a common return cable that provides at least a portion of an electrical path between the return electrode and each of the first and second ESUs.

22. A cable connection system according to claim 19, wherein at least a portion of an insulative outer sheath of the first return cable comprises a different thickness or dielectric constant than other portions of the insulative outer sheath in order to facilitate the non-conductive, capacitive electrical connection between the first and second return cables.

23. A cable connection system according to claim 19, wherein the first and second return cables have different lengths from one another.

24. A cable connection system according to claim 19, wherein each of the first and second return cables is configured to be selectively connectable to the first ESU and/or the second ESU.

25. A cable connection system according to claim 19, further comprising one or more adaptor cables.

26. A cable connection system according to claim 25, wherein the one or more adaptor cables are selectively connectable between one or more of:
  the first return cable and the first ESU;
  the second return cable and the second ESU; and
  the first return cable and the electrosurgical return electrode.

27. A cable connection system according to claim 25, wherein the one or more adaptor cables enables connection between otherwise incompatible connectors.

28. A cable connection system according to claim 19, wherein the first and second return cables are selectively joinable together along at least a portion of their respective lengths.

29. A cable connection system according to claim 28, wherein the first return cable comprises an interior retention area extending along at least a portion of its length and which is configured to have the second return cable selectively disposed therein.

30. A cable connection system according to claim 29, wherein the first return cable comprises an opening along at least a portion of its length and through which the second return cable is selectively insertable into or removable from the interior retention area.

31. A cable connection system according to claim 28, wherein at least a portion of the first return cable has a substantially C-shaped cross-section.

\* \* \* \* \*